(12) United States Patent
Richardson et al.

(10) Patent No.: US 10,714,210 B2
(45) Date of Patent: Jul. 14, 2020

(54) SAMPLE MASS SPECTRUM ANALYSIS

(71) Applicant: Micromass UK Limited, Wilmslow (GB)

(72) Inventors: Keith George Richardson, New Mills (GB); Steven Derek Pringle, Hoddlesden (GB)

(73) Assignee: Micromass UK Limited, Wilmslow (GB)

( * ) Notice: Subject to any disclaimer, the term of this patent is extended or adjusted under 35 U.S.C. 154(b) by 232 days.

(21) Appl. No.: 15/578,076

(22) PCT Filed: May 27, 2016

(86) PCT No.: PCT/GB2016/051570
§ 371 (c)(1),
(2) Date: Nov. 29, 2017

(87) PCT Pub. No.: WO2016/193692
PCT Pub. Date: Dec. 8, 2016

(65) Prior Publication Data
US 2018/0150617 A1    May 31, 2018

(30) Foreign Application Priority Data

May 29, 2015 (GB) .................................. 1509313.1

(51) Int. Cl.
*G16C 20/20* (2019.01)
*G01N 30/72* (2006.01)
(Continued)

(52) U.S. Cl.
CPC .............. *G16C 20/20* (2019.02); *C40B 30/10* (2013.01); *H01J 49/164* (2013.01); *G01N 30/72* (2013.01)

(58) Field of Classification Search
CPC ....... G16C 20/20; G01N 30/72; H01J 49/164; H01J 49/0036; C40B 30/10
See application file for complete search history.

(56) References Cited

U.S. PATENT DOCUMENTS 5,672,869 A * 9/1997 Windig ............... H01J 49/0036
250/282
7,606,667 B2 * 10/2009 Herold .................. G01N 30/72
250/339.07
(Continued)

FOREIGN PATENT DOCUMENTS

EP      2354796 A1    8/2011

OTHER PUBLICATIONS

International Search Report and Written Opinion for PCT/GB2016/051570 dated Sep. 27, 2016.
(Continued)

*Primary Examiner* — Mohamed Charioui

(57) ABSTRACT

A method of analysing a sample mass spectrum comprises comparing a sample mass spectrum of a sample with each reference mass spectrum of plural reference mass spectra. A similarity index is assigned to each reference mass spectrum of the plural reference mass spectra based on similarity between the sample mass spectrum and the reference mass spectrum. For each group of one or more groups of the plural reference mass spectra, the similarity indexes for the reference mass spectra belonging to the group are combined so as to provide a group index for the group at a first level of a hierarchy of sample characteristics. The reference mass spectra belonging to each group are mass spectra of reference samples that have a particular characteristic in common. The method provides a way to categorise a sample as belonging to a particular group of reference samples.

19 Claims, 2 Drawing Sheets

(51) Int. Cl.
*C40B 30/10* (2006.01)
*H01J 49/16* (2006.01)

(56) References Cited

U.S. PATENT DOCUMENTS

| | | | |
|---|---|---|---|
| 7,684,934 B2* | 3/2010 | Shvartsburg | H01J 49/04 |
| | | | 702/27 |
| 9,869,662 B2* | 1/2018 | Kageyama | G01N 30/86 |
| 2010/0248298 A1* | 9/2010 | Kostrzewa | C12C 1/04 |
| | | | 435/34 |
| 2013/0054603 A1* | 2/2013 | Birdwell | G06K 9/6224 |
| | | | 707/738 |

OTHER PUBLICATIONS

Stein, S. E., et al., "Optimization and testing of mass spectral library search algorithms for compound identification", Journal of the American Society for Mass Spectrometry, Elsevier Science Inc., vol. 5, No. 9, p. 859-866, Sep. 1, 1994.

Wan, K. X. et al., "Comparing similar spectra: from similarity index to spectral contrast angle", Journal of the American Society for Mass Spectrometry, Elsevier Science Inc. vol. 13, No. 1, p. 85-88, Jan. 1, 2002.

Horai H., et al., "MassBank: a public repository for sharing mass spectral data for life sciences", Journal of Mass Spectrometry, vol. 45, No. 7, p. 703-714, Jul. 7, 2010.

* cited by examiner

SAMPLE MASS SPECTRUM ANALYSIS

CROSS-REFERENCE TO RELATED APPLICATION

This application is a national phase filing claiming the benefit of and priority to International Patent Application No. PCT/GB2016/051570, filed on May 29, 2016, which claims priority from and the benefit of United Kingdom patent application No. 1509313.1 filed on May 29, 2015. The entire contents of these applications are incorporated herein by reference.

FIELD OF THE INVENTION

The present invention relates generally to mass spectrometry and in particular to a method of analysing a sample mass spectrum, a method of mass spectrometry, a control system for analysing a sample mass spectrum, and a mass spectrometer or mass spectrometer system.

BACKGROUND

Mass spectrometry has been used for the identification of microorganisms (microbes) in cell cultures for many years.

Microbes can be grown on the surface of a solid medium, for example formed by combining liquid agar with appropriate nutrients and the mixture is then allowed to solidify on a sample plate. Samples of microbes are then deposited on the surface of the solid medium and the plate is stored for a period of time in controlled conditions favourable for the growth of the microbes.

The growth conditions for growing a particular sample of microbes, including for example the type and mixture of nutrients provided in the growth medium, the conditions such as temperature in which the microbes are incubated, and the length of time for which the microbes are incubated, can be selected based on one or more factors (e.g. on the type of microbes that are suspected to be present in the sample). One or more additional substances may be added to the growth medium to, for example, suppress the growth of certain microbes or classes of microbe in the sample or to enable easier distinction between the microbe sample from other microorganisms.

The identification of a microbe sample using mass spectrometry usually proceeds by transferring some of the microbe culture from the sample plate onto a mass spectrometry sample plate. A sample mass spectrum of the sample microbe can be obtained by Matrix Assisted Laser Desorption Ionisation ("MALDI") Time of Flight ("ToF") mass analysis. A matrix substance is added to the sample plate which is used in a subsequent ionization by a Matrix Assisted Laser Desorption Ionisation ion source to generate positively charged ions. The generated ions are then mass analysed using a Time of Flight mass analyser. Other types of ionization may be used including ion sources that generate negatively charged ions.

Multiple reference spectra (e.g. 10 or more) corresponding to a known type of microbe are usually acquired and stored. This is performed for a number of different types of microbes to create a library of reference spectra for a plurality of different known types of microbes. The multiple reference spectra of a particular type of microbe are intended to capture variability that arises when acquiring the reference spectra and/or in the experimental parameters.

Such variability arises for a number of reasons. For example, mass spectra acquired for a particular type of microbe may show differences due to factors that cannot be controlled e.g. systematic factors such as chemical, statistical or electrical noise. In addition, a particular microbe may produce significantly different reference mass spectra as a result of variations in conditions that can be controlled e.g. the conditions under which the microbe is grown, differences in the composition of the growth medium on which it is cultured, the length of time for which it is cultured and the temperature at which the culture is stored, etc. amongst many others factors. The individual mass spectrometer used to obtain the mass spectra of the microbe can also contribute to the variability.

It is desirable to incorporate as much of the variability as possible in the library by obtaining and storing as many reference spectra of a particular type of microbe as possible. However, if an excessive number of reference spectra corresponding to a variety of controllable conditions are obtained and incorporated in the library as a single "consolidated" reference spectrum, then mass peaks that are potentially useful for diagnostic purposes may be averaged out or eliminated.

In operation, a sample containing unknown microbes is analysed. Multiple mass spectra (replicates) of the sample are usually obtained and the obtained mass spectra are compared with the reference mass spectra in the library. In one class of identification strategy, a score or an index is assigned to every library entry (reference spectrum) which characterises the agreement or similarity between a reference spectrum and the mass spectrum obtained from the sample and reflects the goodness of fit of the reference spectrum with respect to the sample spectrum. The assigned scores or indices are then used to rank the library entries.

Amongst the reference spectra of a particular type of microbe, it is often arranged that components of the spectra that exhibit less variability contribute more to the score than those that are more variable. These less variable components are deemed to be more informative. Here, a "component" refers to a mass spectrometric peak, a mass region or an individual mass channel. Such selection may be carried out in a soft approach, for example through the use of likelihood of agreement, or in a more hard-edged approach, for example using the variability to select (or discard) peaks to be stored in the library.

US 2008/0300826 (Schweitzer) describes a method of searching a spectral database comprising plural sublibraries in order to identify unknown materials. A search of a sublibrary is performed using a similarity metric that compares a test data set to each reference data set of the sublibrary. The result is a set of probabilities for the sublibrary, with one probability for each reference data set of the sublibrary. This searching process is performed in respect of plural sublibraries, which each relate to a different analytical technique (e.g. Raman spectroscopy, fluorescence spectroscopy, mass spectrometry, etc.), using different sample spectra and reference spectra produced using the different analytical techniques. Corresponding probabilities for a particular reference material that are obtained using the different analytical techniques are then "fused" to give a set of final probabilities. The unknown sample is then classified based on the highest final probability.

GB 2471746 (Maier) describes a method of identifying microbes by comparison of their mass spectra with reference spectra. The method comprises calculating similarity indicators between the reference spectra and a sample spectrum.

US 2011/0202282 (Kostrzewa) discloses a multi stage search algorithm for identifying a sample of microbes wherein a library of reference spectra is divided into a number of sub-libraries, each sub-library being organised according to the frequency of identification of different species of microbes. The structure is used to improve searching speed by first searching through a sub-library of the most frequently identified species of microbes and then through sub-libraries of decreasing frequency.

It is desired to provide an improved method of analysing a sample mass spectrum.

SUMMARY

According to an aspect there is provided a computer-implemented method of analysing a sample mass spectrum, the method comprising:

comparing a sample mass spectrum of a sample with each reference mass spectrum of plural reference mass spectra;

assigning a similarity index to each reference mass spectrum of the plural reference mass spectra based on similarity between the sample mass spectrum and the reference mass spectrum; and for each group of one or more groups of the plural reference mass spectra, combining the similarity indexes for the reference mass spectra belonging to the group so as to provide a group index for the group at a first level of a hierarchy of sample characteristics, wherein the reference mass spectra belonging to the group are mass spectra of reference samples that have a particular characteristic in common.

As discussed above, US 2008/0300826 A1 (Schweitzer) describes a method of searching a spectral database comprising plural sublibraries in order to identify unknown materials. However, in Schweitzer, corresponding probabilities based on different types of sample spectra (e.g. a probability based on a comparison of a Raman sample spectrum with a Raman reference spectrum, a probability based on a comparison of a fluorescence sample spectrum with a fluorescence reference spectrum, a probability based on a comparison of a sample mass spectrum with a reference mass spectrum, etc.), for a particular reference material are "fused" to give a final probability for the particular reference material. This is in contrast to embodiments disclosed herein, in which plural similarity indexes that are generated using the same sample mass spectrum for a sample are combined to give a group index for a group of reference samples that have a particular characteristic in common.

As is also discussed above, GB 2471746 (Maier) describes a method of identifying microbes by comparison of their mass spectra with reference spectra in which similarity indicators between the reference spectra and a sample spectrum are calculated. However, Maier does not describe that the similarity indicators are combined. Instead, a group of reference spectra are selected for further consideration based on the similarity indicators. The further consideration then involves calculating a new set of similarity indicators for the selected reference spectra, taking into account weightings that are determined from and applied to the selected reference spectra, such that one reference spectrum stands out. In contrast to this, embodiments disclosed herein do not seek to single out a reference spectrum, but instead comprise combining similarity indexes for plural reference spectra so as to provide a group index for a group of reference samples that have a particular characteristic in common.

Embodiments disclosed herein also differ from other known conventional methods, such as the approach described in US 2011/0202282 (Kostrzewa), in that by combining the similarity indices of individual reference spectra of a group of reference spectra at a particular level of hierarchy, a group index may be obtained for the group that represents the probability of the sample having the common characteristic of the group.

According to embodiments disclosed herein, combining the similarity indexes for the reference mass spectra belonging to each group into a group index may allow a sample to be categorised as belonging to that group. In embodiments, the sample may be accurately and rapidly categorised as belonging to the group, for example without needing to consider each and every similarity index for the reference mass spectra belonging to that group. In embodiments, the sample may even be categorised in situations where the sample mass spectrum is generally similar to the reference mass spectra of the group, but where the sample mass spectrum is not sufficiently similar to any particular one of the reference mass spectra of that group, for example due to variability in the mass spectra of that group, e.g. caused by varying experimental parameters. Embodiments disclosed herein therefore provide significant advantages over known conventional methods.

In embodiments, the one or more groups of the plural reference mass spectra optionally comprises plural groups of the plural reference mass spectra. The plural groups of the plural reference mass spectra are optionally distinct groups of the plural reference mass spectra (i.e. each of the plural reference mass spectra optionally belongs to only one of the plural groups at the first level of the hierarchy).

According to an embodiment, the method may further comprise, for each group of one or more sub-groups of the plural reference mass spectra, combining the similarity indexes for the reference mass spectra belonging to the group so as to provide a group index for the group at a second level of the hierarchy, wherein the second level of the hierarchy is lower than the first level of the hierarchy, wherein the reference mass spectra belonging to the group are mass spectra of reference samples that have a further particular characteristic in common (e.g. in addition to the particular characteristic referred to above). In embodiments, this hierarchal structure may be repeated mutatis mutandis in respect of one or more further sub-groups of the plural reference mass spectra at further, lower, levels (e.g. a third, a fourth, a fifth, a sixth, etc., level) of the hierarchy.

In embodiments, the sample may be identified as belonging to a group (e.g. a more specific group) at a lower level (e.g. at the second level, at the third level, etc.) of the hierarchy, for example in addition to or instead of being identified as belonging to a group (e.g. a less specific group) at a higher level (e.g. at the first level) of the hierarchy. This may allow for more precise identification of the sample at the lower level if appropriate, yet still conveniently allow for less precise identification of the sample at the higher level.

In embodiments, the one or more sub-groups of the plural reference mass spectra optionally comprises plural sub-groups of the plural reference mass spectra. The plural sub-groups of the plural reference mass spectra are optionally distinct sub-groups of the plural reference mass spectra (i.e. each of the plural reference mass spectra optionally belongs to only one of the groups at each (lower) level of the hierarchy).

In embodiments, one or more of the group indexes at a particular level (e.g. the first level) of the hierarchy may be provided by combining plural of the group indexes at a lower level (e.g. the second level, the third level, etc.) of the hierarchy. This may provide a convenient and efficient way to provide the group indexes at the higher level of the hierarchy.

In embodiments, combining the similarity indexes may comprise adding together the similarity indexes. Similarly, in embodiments, combining the group indexes may comprise adding together the group indexes.

According to an embodiment the similarity indexes may be normalised similarity indexes, for example such that combining the normalised similarity indexes for all of the reference mass spectra results in a predetermined value. The predetermined value may be 1 or 100%. In embodiments, a normalised similarity index closer to 1 or 100% for a reference mass spectrum may indicate that the reference mass spectrum is more likely to identify the sample. In embodiments, a normalised similarity index of 1 or 100% for a reference mass spectrum may indicate that the reference mass spectrum provides an unambiguous identification of the sample. In these embodiments, assigning a similarity index to each reference mass spectrum of the plural reference mass spectra may comprise: assigning an initial similarity index to the reference mass spectrum based on similarity between the sample mass spectrum and the reference mass spectrum; and normalising the initial similarity index so as to provide a normalised similarity index. In embodiments, normalising the similarity index may comprise dividing the initial similarity index by the sum of all of the initial similarity indexes of the plural reference mass spectra.

According to an embodiment the similarity indexes may also or instead be weighted similarity indexes. The weighting may be based on, for example, a known prevalence of the sample type to which the reference mass spectrum relates in a given population. In these embodiments, assigning a similarity index to each reference mass spectrum of the plural reference mass spectra may comprise: assigning an initial similarity index to the reference mass spectrum based on similarity between the sample mass spectrum and the reference mass spectrum; and applying a weighting factor to the initial similarity index so as to provide a weighted similarity index. In embodiments, applying the weighting factor may comprise multiplying the initial similarity index by the weighting factor. The weighting factor may be a prior probability and/or may be based on a known prevalence of the sample type to which the reference mass spectrum relates in a given population.

In embodiments in which a weighted similarity index is provided, the weighted similarity index (rather than the initial similarity index) may be normalised so as to provide the normalised similarity index. Thus, according to an embodiment, assigning a similarity index to each reference mass spectrum of the plural reference mass spectra may comprise: assigning an initial similarity index to the reference mass spectrum based on similarity between the sample mass spectrum and the reference mass spectrum; applying a weighting factor to the initial similarity index so as to provide a weighted similarity index; and normalising the weighted similarity index so as to provide a normalised similarity index.

The (initial, weighted and/or normalised) similarity index for each reference mass spectrum of the plural reference mass spectra may be a probability that the sample is of the sample type to which the reference mass spectrum relates. In embodiments, the (e.g. normalised) similarity index for each reference mass spectrum of the plural reference mass spectra may be a Bayesian probability that the sample is of the sample type to which the reference mass spectrum relates, for example given the plural reference mass spectra and/or given the sample mass spectrum.

According to an embodiment the sample may comprise a culture of microorganisms (microbes). In embodiments, the particular characteristic for each group may be selected from the group consisting of: Gram group (positive or negative); taxonomic classification; genus; species; strain; growth medium; culture time; growth condition; control group; and phylum. In embodiments, each particular characteristic may be placed at a level in the hierarchy based on its specificity and/or interest to the user.

In embodiments, a less specific and/or more interesting characteristic (e.g. genus or Gram group) may be placed at a higher level (e.g. the first level) of the hierarchy and a more specific and/or less interesting characteristic (e.g. strain, control group etc.) may be placed at a lower level (e.g. the second level, the third level, etc.) of the hierarchy. In embodiments, the genus or Gram group may be placed at the highest level (e.g. first level) of the hierarchy. Placing the Gram group at a higher, or the highest, level may allow a rapid and accurate determination to be made regarding whether or not the sample is more receptive to antibiotics. In embodiments, the control group may be placed at the lowest level (e.g. third level) of the hierarchy. Placing the control group at a lower, or the lowest, level may accommodate for variations in experimental parameters used for the control groups.

According to an embodiment the method may further comprise associating the sample with one of the groups based on the group index for that group. In embodiments, the sample may be associated with a group having a group index equal to or above a predetermined threshold value (e.g. a predetermined threshold value for a particular level of the hierarchy). The sample may also or instead be associated with a group having the highest group index of the one or more groups (e.g. the highest group index at a particular level of the hierarchy).

In embodiments, each of the plural reference mass spectra may be obtained from a single known sample or from plural known samples. In embodiments, one or more of the reference mass spectra may comprise a consolidated reference mass spectrum having one or more representative components (e.g. mass peak(s), mass region(s) and/or mass channel(s)) derived from plural replicate mass spectra, optionally together with variability data. The variability data may include information relating to variations in the one or more representative components across the plural replicate mass spectra. The one or more representative components may be derived by averaging one or more components of the plural replicate mass spectra and/or by selecting one or more distinctive components from the plural replicate mass spectra. The plural replicate mass spectra may be obtained from a single known sample or from plural known samples.

In embodiments, the plural reference mass spectra may be stored in a library or database, such as an electronic library or database. The method may comprise retrieving the plural reference mass spectra from the library or database.

In embodiments, the results of the analysis (e.g. one or more similarity indexes, group indexes, associated groups, categorisations, etc., for the sample) may be output, e.g. for storage in a library or database, such as an electronic library or database, or for display by a display device.

According to another aspect there is provided a method of mass spectrometry comprising:
 obtaining a sample mass spectrum from a sample; and
 analysing the sample mass spectrum using a method as described herein.

In embodiments, the method of mass spectrometry may comprise obtaining the sample mass spectrum by performing a MALDI Time of Flight mass analysis on the sample.

In embodiments, the method may be implemented by a control system, for example a control system of or for a mass spectrometer or mass spectrometer system.

According to another aspect there is provided a control system for analysing a sample mass spectrum, wherein the control system is arranged and adapted to:

compare a sample mass spectrum of a sample with each reference mass spectrum of plural reference mass spectra;

assign a similarity index to each reference mass spectrum of the plural reference mass spectra based on similarity between the sample mass spectrum and the reference mass spectrum; and for each group of one or more groups of the plural reference mass spectra, combine the similarity indexes for the reference mass spectra belonging to the group so as to provide a group index for the group at a first level of a hierarchy of sample characteristics, wherein the reference mass spectra belonging to the group are mass spectra of reference samples that have a particular characteristic in common.

The control system described herein may form part of a mass spectrometer or mass spectrometer system.

According to another aspect there is provided a mass spectrometer or mass spectrometer system comprising:

a mass analyser arranged and adapted to obtain a sample mass spectrum from a sample; and a control system as described herein, wherein the control system is arranged and adapted to analyse the sample mass spectrum.

The mass spectrometer or mass spectrometer system may further comprise a library or database, such as an electronic library or database, configured to store the plural reference mass spectra.

The mass spectrometer or mass spectrometer system may further comprise a library or database, such as an electronic library or database, configured to store the results of the analysis (e.g. one or more similarity indexes, group indexes, associated groups, categorisations, etc., for the sample).

The mass spectrometer or mass spectrometer system may further comprise a display device configured to display the results of the analysis (e.g. one or more similarity indexes, group indexes, associated groups, categorisations, etc., for the sample).

According to another aspect there is provided a method of identifying a sample comprising:

comparing a sample mass spectrum with one or more reference spectra stored in a library and assigning each of the compared reference spectrum a similarity index based on similarity between the sample spectrum and the compared reference spectrum; and for one or more levels of hierarchy, calculating a group index for one or more groups of reference spectra at a selected level of hierarchy by combining the similarity index assigned to each reference spectrum belonging to the group.

According to an embodiment, a sample spectrum that is a mass spectrum obtained for a sample, for example of an unknown species of microbes, may be compared with one or more reference spectra that are stored in a library.

Based on the result of the comparison a similarity index may be assigned to each of the compared reference spectrum, wherein the similarity index characterises the similarity between the sample spectrum and each respective reference spectrum. The one or more reference spectra with which the sample spectrum is compared may be arranged into groups according to a predetermined hierarchy.

The levels of hierarchy may be ordered according to experimental (controllable) parameters and/or characteristics, for example according to control groups, culture medium, etc., and the parameter and/or characteristic that is of primary interest may be placed at the top of the hierarchy. Then, for one or more levels of hierarchy, a group index may be calculated for one or more groups of reference spectra at a selected level of hierarchy (e.g. a selected experimental parameter and/or characteristic of interest) by combining the similarity index assigned to each reference spectrum that belongs to the respective group.

According to embodiments, it is possible to obtain similarity (probability) information simultaneously at one or more levels of hierarchy e.g. phylum, genus, species, growth conditions. This way, even when results are inconclusive at a lower level of the hierarchy (e.g. when the combined indices of every group at the "species" level are comparable to each other) useful information may still be obtained at a higher level of the hierarchy e.g. at the "genus" level.

Moreover, it is possible to provide a more consistent and more accurate way of dealing with variability seen in mass spectra arisen from variations in experimental parameters, such as growth medium or culture time, which may otherwise reduce the level of confidence in the search results or may require filtering of the library to be searched.

The sample to be identified may be a sample culture of microorganisms.

The similarity indices of the reference spectra belonging to a group may be combined to obtain a group index by adding together the similarity index of each reference spectrum belonging to the group.

In embodiments, a level of hierarchy corresponds to a Gram group (positive or negative), taxonomic classification, genus, species, strain, growth medium, culture time, growth conditions, control group or phylum.

In some embodiments, the lowest level of hierarchy amongst the one or more levels of hierarchy may correspond to control group.

In embodiments, the one or more levels of hierarchy are organised in order of specificity and/or in order of experimental parameters and/or characteristics of interest.

In some embodiments, the experimental parameters and/or characteristics may comprise one or more of Gram group (positive or negative), taxonomic classification, genus, species, strain, growth medium, culture time, growth conditions, control group or phylum.

In some embodiments, the sample may be identified with a group at a level of hierarchy that has a group index equal to or above a predetermined threshold value.

In some embodiments, the sample may be identified with a group at a level of hierarchy that has a group index that is highest at that level of hierarchy.

According to another aspect there is provided a method of mass spectrometry comprising a method of identifying a sample as described herein.

An embodiment provides a method of mass spectrometry that comprises a method as described herein, wherein the method may comprise obtaining the sample mass spectrum of the sample to be identified by performing a MALDI Time of Flight mass analysis on the sample.

According to another aspect there is provided a control system of a mass spectrometer or mass spectrometer system, wherein the control system is arranged and adapted:

(i) to compare a sample mass spectrum of the sample with one or more reference spectra stored in a library and assign each of the compared reference spectrum a similarity index based on similarity between the sample spectrum and the compared reference spectrum; and (ii) for one or more levels of hierarchy, to calculate a group index for one or more groups of reference spectra at a selected level of hierarchy by combining the similarity index assigned to each reference spectrum belonging to the group.

The sample may comprise a sample culture of microorganisms.

Combining the similarity index of each reference spectrum of the group may comprise adding the similarity index of each reference spectrum belonging to the group.

The one or more levels of hierarchy may correspond to one or more of Gram group (positive or negative), taxonomic classification, genus, species, strain, growth medium, culture time, growth condition, control group and phylum.

The lowest level of hierarchy amongst the one or more levels of hierarchy may correspond to a control group.

The one or more levels of hierarchy may be organised in order of specificity and/or in order of experimental parameters and/or characteristics of interest.

The experimental parameters and/or characteristics may comprise one or more of Gram group (positive or negative), taxonomic classification, genus, species, strain, growth medium, culture time, growth condition, control group and phylum.

The sample may be identified with a group at a level of hierarchy that has a group index equal to or above a predetermined threshold value.

The sample may be identified with a group at a level of hierarchy that has a group index that is highest at that level of hierarchy.

According to another aspect there is provided a mass spectrometer or mass spectrometer system comprising a control system as described herein.

According to another aspect there is provided a method of searching a microbe mass spectrometry database in which the search results are hierarchical in structure and wherein scores at higher levels in the hierarchy can be calculated by combining scores at lower levels of the hierarchy.

According to an embodiment the mass spectrometer or mass spectrometer system may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap;

(iv) a Penning ion trap; (v) an ion trap; (vi) a magnetic sector mass filter; (vii) a Time of Flight mass filter; and (viii) a Wen filter; and/or (k) a device or ion gate for pulsing ions; and/or (l) a device for converting a substantially continuous ion beam into a pulsed ion beam.

The mass spectrometer or mass spectrometer system may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer or mass spectrometer system further comprises a device arranged and adapted to supply an AC or RF voltage to the electrodes. The AC or RF voltage optionally has an amplitude selected from the group consisting of: (i) about <50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) >about 500 V peak to peak.

The AC or RF voltage may have a frequency selected from the group consisting of: (i) <about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (xxv) >about 10.0 MHz.

The mass spectrometer or mass spectrometer system may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar; and (ix) >about 1000 mbar.

According to an embodiment analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv)

dibenzothiophene; (xvi) 1,10'-phenanthroline; (xvii) 9'anthracenecarbonitrile; and (xviii) anthraquinone; and/or (c) the reagent ions or negatively charged ions comprise azobenzene anions or azobenzene radical anions.

According to an embodiment the process of Electron Transfer Dissociation fragmentation comprises interacting analyte ions with reagent ions, wherein the reagent ions comprise dicyanobenzene, 4-nitrotoluene or azulene.

BRIEF DESCRIPTION OF THE DRAWINGS

Various embodiments will now be described, by way of example only, and with reference to the accompanying drawings in which.

DETAILED DESCRIPTION

Figure 1:
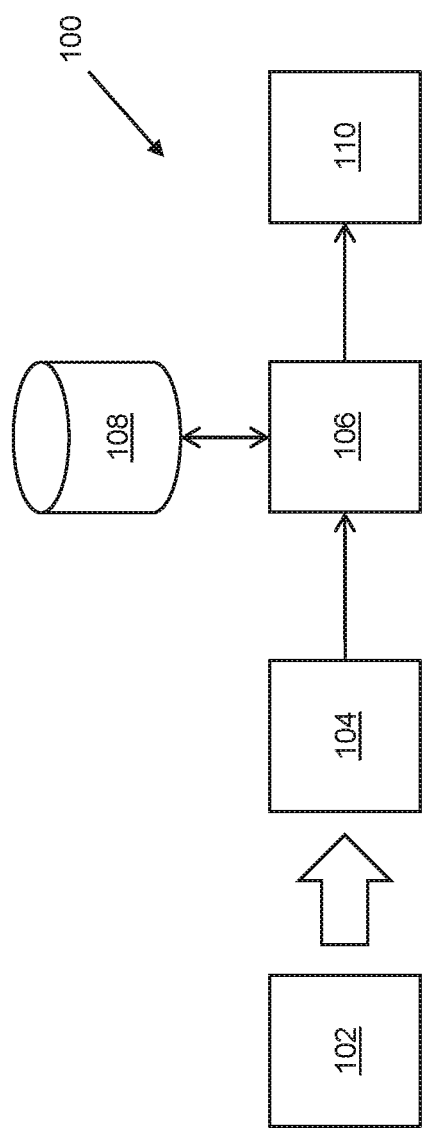
FIG. 1 shows schematically a mass spectrometer system according to an embodiment.

According to an embodiment, a sample mass spectrum is obtained for a sample of an unknown species of microbes. The sample mass spectrum is then compared with each one of plural reference spectra that are stored in a library. Based on the result of the comparison, a similarity index is assigned to each of the compared reference spectrum, wherein the similarity index characterises the similarity between the sample spectrum and each respective reference spectrum.

The reference spectra with which the sample spectrum is compared are arranged into groups according to a predetermined hierarchy, and the levels of hierarchy are ordered according to experimental (controllable) parameters and/or characteristics of interest, wherein the characteristic that is of primary interest is placed at the highest level of the hierarchy. Then, for one or more levels of hierarchy, a group index may be calculated for one or more groups of reference spectra at a selected level of hierarchy (e.g. by selecting an experimental parameter and/or characteristic of interest) and the group index of a group may be obtained by combining the similarity index assigned to each reference spectrum that belongs to the group.

According to this embodiment, variability in the spectra of different species of microbes can be addressed by the hierarchical structure of the reference spectra library. In particular, reference spectra at the lowest level of the hierarchy (e.g. replicates acquired under identical controlled conditions) may be "consolidated" and variability of the individual components (e.g. mass peak, mass region or mass channel) of replicate reference spectra may be calculated. The term "reference mass spectrum" used herein may refer to this consolidated reference mass spectrum together with the calculated variabilities.

Direct scoring to assign a similarity index to individual reference mass spectra may be performed only at the lowest level, and scoring at the higher levels in the hierarchy may be performed by combining the similarity indices of individual reference mass spectra from lower levels.

According to embodiments, the one or more levels of hierarchy may correspond to experimental parameters and/or characteristics of interest, which may include one or more of Gram group (positive or negative), taxonomic classification, genus, species, strain, growth medium, culture time, growth conditions, control group and phylum. In embodiments, the parameter and/or characteristics of primary interest is placed at the top of the hierarchy. Thus, for example, the higher levels of the hierarchy may correspond to one or more different types of classification such as taxonomic classifications, while the lowest level may correspond to different control groups.

In an embodiment, a similarity index that is assigned to each of the reference mass spectra based on a comparison between the reference mass spectra and the sample mass spectrum characterises the similarity between respective reference spectra and the sample mass spectrum. In probabilistic language, the similarity index assigned to a reference spectrum represents the probability of the sample mass spectrum given the reference mass spectra. These similarity indices may be combined additively to obtain a group index for a group of reference spectra that share one or more common characteristics e.g. a group of reference spectra that are obtained under the same or similar controlled conditions. The similarity indexes may be derived from initial similarity indexes or "likelihoods" which may be multiplied by a weighting factor or "prior probability" and then normalised. If the similarity indices are normalised so as to sum to 1 or 100%, then each similarity index and group index in effect represents the Bayesian probability of the sample mass spectrum given the reference mass spectra.

FIG. 1 shows schematically a mass spectrometer system 100 that can be used to obtain and analyse a sample mass spectrum according to an embodiment.

In this embodiment, the mass spectrometer system 100 comprises an ion source 102, a mass analyser 104, a control system 106, an electronic storage device 108 and a display device 110.

In this embodiment, sample analyte ions are generated by Matrix Assisted Laser Desorption Ionisation (MALDI) in the ion source 102. However, ions may be generated in any other desired and suitable way from the sample.

The ions are then transferred from the ion source 102 to the mass analyser 104. In this embodiment, the mass analyser 104 comprises a TOF mass analyser that generates a sample mass spectrum having plural mass spectral peaks. The mass spectrometer system 100 can also or instead comprise any desired and suitable device or devices that a mass spectrometer may have, such as one or more ion guides, ion mobility or differential ion mobility separation devices, ion traps, collision, fragmentation or reaction cells, mass filters, mass analysers, ion detectors, etc.

The sample mass spectrum is then analysed by a control system 106 in the manner described herein. The control system 106 can comprise any desired and suitable processing circuitry, such as dedicated processing circuitry that is suitably configured or controlled (e.g. in hardware) to perform the analysis and/or general purpose processing circuitry that is suitably configured and controlled (e.g. by software) to perform the analysis.

The analysis is carried out using data for reference mass spectra stored in a library in the electronic storage device 108 that is accessible to the control system 106.

The results of the analysis (e.g. one or more similarity indexes, group indexes, associated groups and/or categorisations) are then output by the control system 106 for storage in the electronic storage device 108 and/or for display by the display device 110.

As will be appreciated, the arrangement shown in FIG. 1 is just one example of many possible arrangements to which the concepts described herein may equally be applied.

Figure 2:
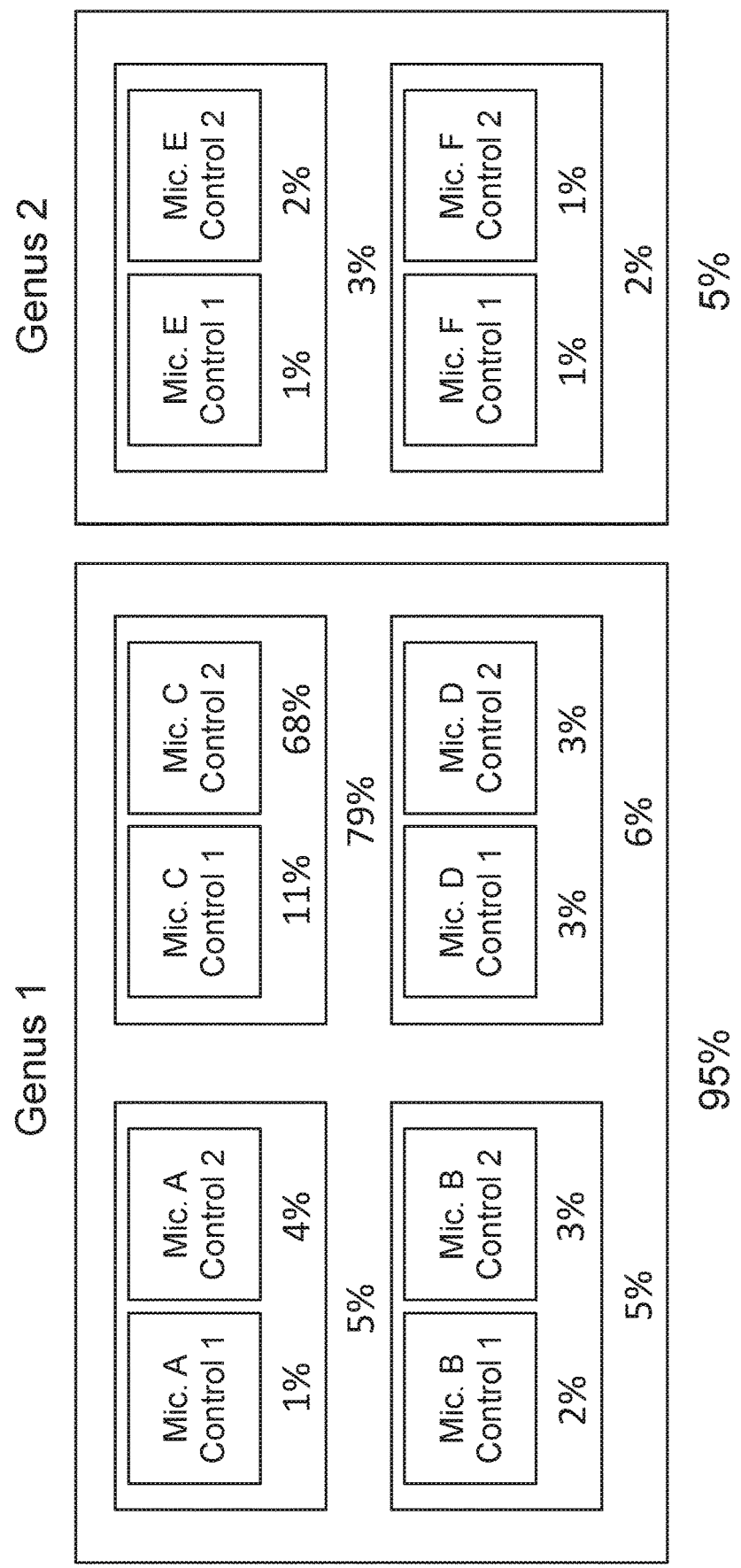
FIG. 2 shows similarity indexes and group indexes provided in accordance with an embodiment.

An example illustrating an embodiment of the analysis method is shown in FIG. 2 and will be described in more detail. According to the embodiment shown in FIG. 2 reference mass spectra are compared with a sample spectrum obtained from a sample of unknown microbes. Similarity indices representing the probabilities of agreement with the sample mass spectrum are determined using component variability from replicates reference spectra (reference spectra obtained under identical controlled conditions) within each control group, and the determined similarity indices are assigned to the individual control groups. The similarity indices (probabilities) of a group of reference spectra that share a common characteristic (defined by the experimental parameter and/or characteristic of interest at a higher level, e.g. species) may then simply be added together to obtain a group index for a group of reference mass spectra at the higher level of the hierarchy. Such hierarchical scoring structure can provide a convenient way to summarise the results.

As shown in FIG. 2, at the lowest level of a hierarchy set up for a library of reference spectra, the library may be divided according to control groups, "Control 1" and "Control 2", for each species of microbes A, B, C, D, E and F, and the reference mass spectrum of each group is compared with a sample spectrum and assigned a similarity index (score) that represents the probability that the sample is of the sample type to which the reference mass spectrum relates. For example, Control 1 of microbe A is assigned a similarity index of 1%, Control 2 of microbe A is assigned a similarity index of 4%, etc.

At a higher level, the library is divided into groups of reference mass spectra according to species, and a group index for each group is calculated by adding the similarity indices assigned to both Control 1 and Control 2 of each species. For example, the group index for microbe A is the sum of 1% for Control 1 and 4% for Control 2 which is 5%, and the group index for microbe B is the sum of 2% for Control 1 and 3% for Control 2 which is 5%, etc.

At the highest level, the library is divided according to genus. A group index for each of genus 1 and genus 2 is calculated by adding the group indices of all species groups that belong to the genus. For example, the group index for genus 1 is the sum of 5% for microbe A, 5% for microbe B, 79% for microbe C and 6% for microbe D which is 95%, and the group index for genus 2 is the sum of 3% for microbe E and 2% for microbe F which is 5%.

Since the similarity indices represent the probability of a match with the sample spectrum, as can be seen from FIG. 2, at each level of hierarchy, the sum total of the similarity indices of all groups is 100%.

The similarity indices can also be manipulated according to the rules of probability. Thus, the result can be represented as:

| Level 1 | Level 2 | Level 3 |
|---|---|---|
| Pr(Genus 1) = 95% | Pr(Mic. A\|Genus 1) = 5.3% | Pr(Control 1\|Mic. A, Genus 1) = 20% Pr(Control 2\|Mic. A, Genus 1) = 80% etc. |
|  | Pr(Mic. B\|Genus 1) = 5.3% |  |
|  | Pr(Mic. C\|Genus 1) = 83.2% |  |
|  | Pr(Mic. D\|Genus 1) = 6.3% |  |
| Pr(Genus 2) = 5% | Pr(Mic. E\|Genus 2) = 60% |  |
|  | Pr(Mic. F\|Genus 2) = 40% |  |

Here, Pr(A|B) denotes the probability of A given B, and Pr(A|B,C) denotes the probability of A given B and C.

It should be noted that, although the levels of hierarchy in this embodiment are divided according to particular experimental parameters and/or characteristics, other ways of dividing the library of reference spectra are also possible and the levels of hierarchy may be organised in any way as desired or required.

Different hierarchies may also be set up, and more than one hierarchy may be set up for a given sample of unknown microbes, such that different experimental parameters and/or characteristics may be interrogated simultaneously using the same set of data. For example, culture medium may be placed at the top of the hierarchy in one embodiment if it is the parameter and/or characteristic of primary interest. In another embodiment, Gram group may be placed at the top of the hierarchy.

Although the present invention has been described with reference to various embodiments, it will be understood by those skilled in the art that various changes in form and detail may be made without departing from the scope of the invention as set forth in the accompanying claims.

The invention claimed is:

1. A computer-implemented method of analysing a sample mass spectrum of a sample to categorize the sample as being associated with a particular group or being associated with a particular characteristic, the method comprising:
   comparing a sample mass spectrum of a sample with each reference mass spectrum of plural reference mass spectra to determine similarity between the sample mass spectrum and the reference mass spectrum;
   assigning a similarity index to each reference mass spectrum of the plural reference mass spectra based on the determined similarity between the sample mass spectrum and the reference mass spectrum;
   for each group of one or more groups of the plural reference mass spectra, combining the similarity indexes for the reference mass spectra belonging to the group so as to provide a group index for the group at a first level of a hierarchy of sample characteristics, wherein the reference mass spectra belonging to the group are mass spectra of reference samples that have a particular characteristic in common;
   associating the sample with a group of the one or more groups based on the group index for that said group, wherein the reference mass spectra belonging to said group are mass spectra of reference samples that have a first particular characteristic in common; and
   outputting an indication that at least one of:
      the sample is associated with the first particular characteristic, and
      the sample is associated with said group.

2. A method as claimed in claim 1, further comprising:
   for each group of one or more sub-groups of the plural reference mass spectra, combining the similarity indexes for the reference mass spectra belonging to the group so as to provide a group index for the group at a second level of the hierarchy, wherein the second level of the hierarchy is lower than the first level of the hierarchy, wherein the reference mass spectra belonging to the group are mass spectra of reference samples that have a further particular characteristic in common.

3. A method as claimed in claim 2, wherein one or more of the group indexes at the first level of the hierarchy is provided by combining plural of the group indexes at the second level of the hierarchy.

4. A method as claimed in claim 1, wherein combining the similarity indexes comprises adding together the similarity indexes.

5. A method as claimed in claim 1, wherein the similarity indexes are normalized similarity indexes, such that combining the normalized similarity indexes for all of the plural reference mass spectra results in a predetermined value.

6. A method as claimed in claim 5, wherein the predetermined value is 1 or 100%.

7. A method as claimed in claim 1, wherein the similarity index for each reference mass spectrum of the plural reference mass spectra comprises a probability that the sample is of the sample type to which the reference mass spectrum relates.

8. A method as claimed in claim 1, wherein assigning a similarity index to each reference mass spectrum of the plural reference mass spectra comprises:
assigning an initial similarity index to the reference mass spectrum based on similarity between the sample mass spectrum and the reference mass spectrum; and
applying a weighting factor to the initial similarity index so as to provide the similarity index.

9. A method as claimed in claim 1, wherein the sample comprises a culture of microorganisms.

10. A method as claimed in claim 1, wherein the particular characteristic for each group is selected from the group consisting of: Gram group; taxonomic classification; genus; species; strain; growth medium; culture time; growth condition; control group; and phylum.

11. A method as claimed in claim 1, wherein the sample is associated with a group having a group index equal to or above a predetermined threshold value.

12. A method as claimed in claim 1, wherein the sample is associated with a group having the highest group index of the one or more groups.

13. A method of mass spectrometry comprising:
obtaining a sample mass spectrum from a sample; and
analysing the sample mass spectrum using a method as claimed in claim 1.

14. A method as claimed in claim 13, comprising obtaining the sample mass spectrum by performing a MALDI Time of Flight mass analysis on the sample.

15. A control system for analysing a sample mass spectrum, wherein the control system comprises a processing circuit arranged and adapted to perform a method as claimed in claim 1.

16. A mass spectrometer or mass spectrometer system comprising:
a mass analyser arranged and adapted to obtain a sample mass spectrum from a sample; and
a control system as claimed in claim 15, the control system being arranged and adapted to analyse the sample mass spectrum.

17. A method as claimed in claim 1, wherein outputting the indication comprises outputting the group index for said group that is associated with the sample.

18. A method as claimed in claim 1, wherein outputting the indication comprises storing the indication in a non-transitory computer memory.

19. A method as claimed in claim 1, wherein the method is performed automatically by a processing circuit of a control system.

* * * * *